(12) United States Patent
Jurvelin et al.

(10) Patent No.: US 8,679,019 B2
(45) Date of Patent: Mar. 25, 2014

(54) METHOD FOR MEASURING OF THICKNESSES OF MATERIALS USING AN ULTRASOUND TECHNIQUE

(75) Inventors: Jukka Jurvelin, Kuopio (FI); Ossi Riekkinen, Kuopio (FI); Mikko Hakulinen, Kuopio (FI)

(73) Assignee: Bone Index Finland Oy, Vuorela (FI)

( * ) Notice: Subject to any disclaimer, the term of this patent is extended or adjusted under 35 U.S.C. 154(b) by 761 days.

(21) Appl. No.: 11/999,084

(22) Filed: Dec. 3, 2007

(65) Prior Publication Data

US 2009/0143681 A1 Jun. 4, 2009

(51) Int. Cl.
A61B 8/00 (2006.01)

(52) U.S. Cl.
USPC .............. 600/449; 600/438; 600/442

(58) Field of Classification Search
USPC .............. 600/437, 438, 442, 449; 73/584, 73/588–589, 596–597, 599, 601–602, 620, 73/627–629
See application file for complete search history.

(56) References Cited

U.S. PATENT DOCUMENTS

| 4,512,195 | A |  | 4/1985 | Miwa et al. ............. 73/602 |
| 5,361,767 | A | * | 11/1994 | Yukov ............. 600/442 |
| 5,941,825 | A |  | 8/1999 | Lang et al. ............. 600/449 |
| 6,468,215 | B1 | * | 10/2002 | Sarvazyan et al. ........... 600/438 |
| 6,494,097 | B1 | * | 12/2002 | Shihadeh ............. 73/602 |

FOREIGN PATENT DOCUMENTS

| GB | 2 257 253 A | 1/1993 |
| JP | 2000 237189 | 9/2000 |
| JP | 2001 128973 | 5/2001 |

OTHER PUBLICATIONS

"Dual-Frequency Ultrasound-New Pule-Echo Technique for Bone Densitometry", O. Riekkinen et al., Ultrasound in Med. & Biol., vol. 34, No. 10, pp. 1703-1708, 2008.
"Dual-Frequency Ultrasound Technique Minimizes Errors Induced by Soft Tissue in Ultrasound Bone Densitometry", J. Karjalainen et al., Informa UK Ltd., Oct. 2008, pp. 1038-1041.
"Development and Application of Ultrasound Backscatter Methods for the Diagnostics of Trabecular Bone", Ossi Riekkinen, 84 pgs., 2008.

* cited by examiner

*Primary Examiner* — Unsu Jung
*Assistant Examiner* — Rajeev Siripurapu
(74) *Attorney, Agent, or Firm* — Harrington & Smith (57) ABSTRACT

The invention relates to a method for measuring thicknesses of materials of multilayered structure. This method includes transmitting one or more ultrasound signals including different frequencies into a multilayered structure consisting of two or more materials with one or more ultrasound transducers, measuring materials, acoustic properties for which are different at the frequencies in use, measuring ultrasound signals reflected from the front surface and back surface of the multilayered structure with one or more ultrasound transducer and determining thicknesses of the materials within multilayered structure from the reflected ultrasound signals.

6 Claims, 9 Drawing Sheets

METHOD FOR MEASURING OF THICKNESSES OF MATERIALS USING AN ULTRASOUND TECHNIQUE

FIELD OF INVENTION

The invention relates to a method for measuring thicknesses of materials using an ultrasound technique. Especially the invention relates to a method for the measurement of compositions and thicknesses of two or more multilayered materials with known acoustic properties (i.e. attenuation and speed of sound).

BACKGROUND

Ultrasound consists of propagating mechanical oscillation with a frequency (>20 kHz) exceeding hearing range. Longitudinal waves are generally used in medical ultrasound applications. The longitudinal wave can propagate through all types of media, gases, fluids and solids, which makes it useful in various applications. As the ultrasound travels through a medium, it becomes attenuated due to absorption, reflection and scattering. Thus, material properties of the medium alters the characteristics of the ultrasound propagation and recorded ultrasound signal can be used to evaluate material properties.

In many applications, ultrasound has to travel through unknown composition of acoustically known materials before reaching the region of interest (the object under evaluation). In these cases, the effect of overlaying materials has to be considered and eliminated prior to successful ultrasound evaluation of the object of interest. As an example, diagnostic evaluation of bone using ultrasound necessitates conduction of the ultrasound measurement through the soft tissues overlying bones.

Many industrial processes depend on the measurement of composition and thicknesses of two or more materials. Commercially available ultrasound thickness meters measure thicknesses of two or more materials but these techniques need acoustically visible interfaces (i.e. ultrasound reflections) between different material layers and the prior knowledge of the order of materials in the layered structure. A close monitoring of material characteristics can increase efficiency and improve the product quality. Additional benefits are likely to occur, if such measurements can be accomplished rapidly and in a non-destructive way with acceptable accuracy and precision. Material properties are traditionally measured by some form of destructive analysis (sample separation, peeking) but may be analysed acoustically by using ultrasound measurement and signal analysis.

DESCRIPTION OF THE RELATED ART

The accurate ultrasound measurement of bone properties, such as bone quality and quantity, has long been sought in medical science. The availability of such measurement techniques would allow continuous screening of large patient groups accurately and in repeatable fashion without the use of ionizing radiation (i.e. dual energy X-ray absorptiometry, DXA, at the moment the "golden standard" technique). However, in order to improve diagnostic value of quantitative ultrasound techniques the measurement should be conducted from typical fracture sites, e.g. proximal femur or vertebra. Such anatomical locations are, nevertheless, challenging due to the large amount of soft tissue overlying the bone and interfering the ultrasound evaluation of bone.

In osteoporosis diagnostics, most clinical quantitative ultrasound (QUS) devices are based on through-transmission measurement of calcaneus, which is not a typical fracture site. In contrast to through-transmission measurements, reflection and backscattering measurements may be conducted at typical fracture sites such as vertebra and proximal femur. The variable thickness and composition of soft tissue layer surrounding skeletal bones have a significant undesired effect on bone ultrasound measurements. Earlier, the soft tissue induced errors were found significant being typically between 4 and 130%.

Body composition measurements are typically measured by using a set of measurement calipers to measure the skinfold thickness in multiple sites of the body, using underwater weighting or bioelectric impedance method. Local soft tissue compositions are typically determined with DXA or MRI-technique that are non-invasive but however, involve ionizing radiation (i.e. DXA) and the instruments are expensive and massive (DXA and MRI). The advantage of the ultrasound technique is related to its low price, small portable size and non-ionizing measurement principle. It would be advantageous if local measurements can be accomplished non-invasively with acceptable accuracy and precision using a portable low cost instrument.

Previously, specific multi-frequency approaches have been introduced in patent applications JP 2000-237189 and JP 2001-128973. However, these techniques are based on through-transmission (TT)-geometry that restricts the use of the technique. Further, these techniques assume that ultrasound attenuation is linearly related to frequency. For example, use of TT-geometry in case of bone evaluation from proximal femur (typical osteoporotic fracture site) is challenging due to the extensive attenuation that occurs when ultrasound travels through hip. In addition, the patent GB 2257253 related to ultrasound bone analyzer is also based on TT-measurement geometry. The soft tissue correction method used in this technique (GB 2257253) is based on multiple reflections from adipose-lean-bone interfaces. This is very challenging especially in cases where no clear interfaces are found between e.g. lean and adipose (fat) tissues Moreover, U.S. Pat. No. 5,941,825 of the determination of body fat by using ultrasound is based on the reflections from different soft tissue layers. This is problematic in cases where no clear ultrasound echoes are found between e.g. lean and adipose tissues. U.S. Pat. No. 4,512,195 introduces the ultrasonic living body tissue characterization method that is based on ultrasound reflections from tissue interfaces and different frequencies in order to eliminate soft tissue induced error in ultrasound evaluation. The method uses predetermined constant speed of sound values in all tissues. Soft tissue correction is thereby based on predetermined single speed of sound value and reflections from tissue interfaces. Constant speed of sound value can cause errors in case where real speed of sound values between different tissues are different. Moreover, the method requires acoustically visible tissue interfaces that are in many cases challenging to achieve.

SUMMARY

The object of the invention is to provide a method for measuring thicknesses of materials using an ultrasound technique. With the method, disadvantages related to previous methods are eliminated. The object of the invention is also to provide a method for measuring of compositions and thicknesses of two or more multilayered materials, with known acoustic properties (i.e. attenuation and speed of sound). Furthermore the object of the invention is to provide a method, which can be used in quantitative characterization of natural or engineered multilayer materials. Especially the object of the invention is to provide a method, which is capable of determining the amount and composition of the soft tissue overlying the bone and thus it can enhance accuracy of clinical bone ultrasound measurements significantly.

According to the present invention thicknesses of materials of multilayered structure are measured by transmitting one or more ultrasound signals including different frequencies into a multilayered structure consisting of two or more materials using one or more ultrasound transducers, measuring materials, acoustic properties of which are different for the frequencies in use, measuring ultrasound signals reflected from the front surface and back surface of the multilayered structure with one or more ultrasound transducer and determining the thicknesses of the materials within multilayered structure from the reflected ultrasound signals. As the method is based only on reflections from the acoustically visible front and back surfaces other interfaces within the multilayer material, even when acoustically nonvisible, do not inconvenience the measurements.

The method is capable of determining the amount and composition of overlying soft tissue and thus it can enhance accuracy of clinical ultrasound measurements significantly. Particularly the invention can be applied to eliminate soft tissue effects on bone measurements. As the method is based only on reflection from the bone-soft tissue interface (that is acoustically highly visible) other tissue interfaces without ultrasound echoes do not impair the measurements. The method can be used to evaluate the local soft tissue composition accurately and in a reproducible manner. In addition, the method can be used in quantitative characterization of natural or engineered multilayer materials.

According to an embodiment of the invention the method comprises measuring materials, the values of ultrasound attenuation coefficients and speed of sound of which are known at the frequencies in use. Multilayered materials, without true acoustic reflection in internal layer interfaces, can be assessed for layer thicknesses with a pulse-echo technique.

According to an embodiment of the invention the method comprises transmitting one or more ultrasound signals including different frequencies using one ultrasound transducer and measuring reflected ultrasound signals with the same transducer and observing two or more ultrasound frequencies. The method enables advantageously a measurement system with a single broadband transducer that acts as a transmitter and a receiver in material or tissue characterization.

According to a further embodiment of the invention the method comprises transmitting two or more ultrasound signals with different frequencies using two or more ultrasound transducers and measuring reflected ultrasound signals with two or more transducers and observing two or more ultrasound frequencies. Advantageously, the method enables a measurement system with two narrowband transducers, which give reflection information on material or tissue characterization at different frequencies.

According to a further embodiment of the invention the method comprises measuring thicknesses of biological tissues. The method enables diagnostic and monitoring of body tissues formed by two or more layers with specific acoustic properties According to a further embodiment of the invention the method comprises measuring thicknesses of lean and adipose tissues in a soft tissue. The method evaluates the local soft tissue composition, consisting of lean and adipose tissues, accurately. Monitoring of soft tissue composition can help to evaluate effect of medical treatments and increase efficiency and improve quality of follow up studies. See examples 1 and 2.

According to a further embodiment of the invention the method comprises measuring and correct the effect of overlying soft tissue on acoustic measurement of bone. As the soft tissue can be simplified to consist of adipose and lean tissues with known acoustic properties, the present technique can be applied to eliminate soft tissue effects on bone measurements. Elimination of soft tissue effects will improve accuracy of the measurement of diagnostic bone parameters. See examples 1 and 2.

According to a further embodiment of the invention the method comprises measuring material thicknesses of multilayered structures of a wall. The method can be used to analyse and control quality of different kind wall-like structures consisting of several layers. Such information on the wall structure will help engineers to follow e.g. wall erosion and estimate mechanical integrity of the wall-like structures. Moreover, the information on the thicknesses of the wall-like structure layer enables real-time, non-destructive, quality control of the wall-like structure.

According to a further embodiment of the invention the method comprises measuring thicknesses of coatings overlaying a structure. In many applications, coating integrity, homogeneity and thickness is critical information that is related to functional performance of the coating and the method helps (i.e. providing information on coating thickness) to optimize manufacturing processes as well as enables quality control of coated products.

According to a further embodiment of the invention the method comprises measuring thicknesses of coat paints overlaying a structure. Coat paint integrity, homogeneity and thickness is critical information that is related to functional performance of the coat paint (e.g. mechanical wear resistance) and the method helps (i.e. providing information on coat paint thickness) to optimize manufacturing processes (e.g. optimized coat paint consumption, technical performance optimization) as well as enables quality control of painted products ensuring constant quality between batches.

According to a further embodiment of the invention the method comprises measuring thicknesses of individual layers in natural or man-made structures, typically layered composites consisting e.g. of wood, rubber, plastic, ceramics or concrete. Thereby, the method provides a novel non-destructive material characterization of layered structures, typically needed for applications in e.g. aerospace, automotive and consumer product technology. The method helps to optimize manufacturing processes as well as enables quality control of layered products.

According to a further embodiment of the invention the method comprises measuring and correct the effect of multilayer structure on acoustic measurement of the object of interest that is located behind the multilayer structure. As the multilayer structure can be simplified to consist of two or more materials with known acoustic properties, the present technique can be applied to eliminate multilayer structure effects on the object measurements. Elimination of multilayer structure effects will improve accuracy of the measurement of the object of interest parameters. See examples 1 and 2.

The dual frequency ultrasound technique (DFUS) or multi frequency ultrasound technique (MFUS)) of the present invention is a novel computational technique for determining unknown compositions and thicknesses of two or more multilayered, acoustically known materials.

DFUS technique is based on the pulse-echo geometry in which the same transducer transmits and receives the ultrasound signal. Multiple frequencies, number of those equal to number of different material layers in structure, needed in DFUS or MFUS, can be produced with a single broadband ultrasound transducer or using multiple ultrasound transducers with different frequencies. The present computational method necessitates that the specific acoustic properties of the investigated materials are known, i.e. 1) the values of ultrasound attenuation coefficients for the materials are known and they are frequency dependent, 2) the values of ultrasound attenuation coefficients are different for each material layer and 3) speed of sound for each material is known. When conditions 1-3 are fulfilled, the total thicknesses of each material component in the multilayer material can be determined. The analysis is based on the frequency independent sound reflection from the bottom interface of the multilayer structure. The analysis exploits the time difference between the upper surface reflection and bottom interface reflection of the multilayer structure. Using this information the thickness of each material in multilayer structure can be determined and the composition of the multilayer structure evaluated. The mathematical derivation of DFUS solution is presented in Example 1 (The MFUS solution can be derived analogously). As DFUS-technique is based on the reflection from the bottom of the multilayer structure (can be set to be acoustically highly visible), the acoustically visible reflections from different layers within the multilayered structure are not needed. Thus, the technique can be used to determine composition and thicknesses of the multilayer structure in materials with acoustically non-visible layer structure.

BRIEF DESCRIPTION OF THE FIGURES

FIG. 8 shows mean integrated reflection coefficient (IRC) values as determined with a DFUS correction and without correction in accordance with the example 2, and In FIG. 1 layered material is measured with a single broadband ultrasound transducer. Ultrasound propagates through the multilayered material and is reflected from the bottom of the multilayer structure. The measured pulse-echo signal is recorded for the analysis. The reflection from the bottom of multilayer material is used and compared to the reflection from the reference reflector (standardized reflector such as smooth metal plate). Frequency response of the ultrasound signal (frequency spectrum) is calculated for both signals (material and reference measurements) using the fast Fourier transform (FTT) algorithm. The reflection coefficient is calculated as a ratio between the ultrasound reflection from the bottom of the material and the standard reflector. From the reflection coefficient spectrum, two representative frequencies are determined ($\Delta f1$ and $\Delta f2$) and the corresponding reflection coefficient values (single or mean value) are used for the DFUS-based thickness calculation. Using the DFUS technique, total thicknesses of material 1 and 2 can be determined.

Figure 1:
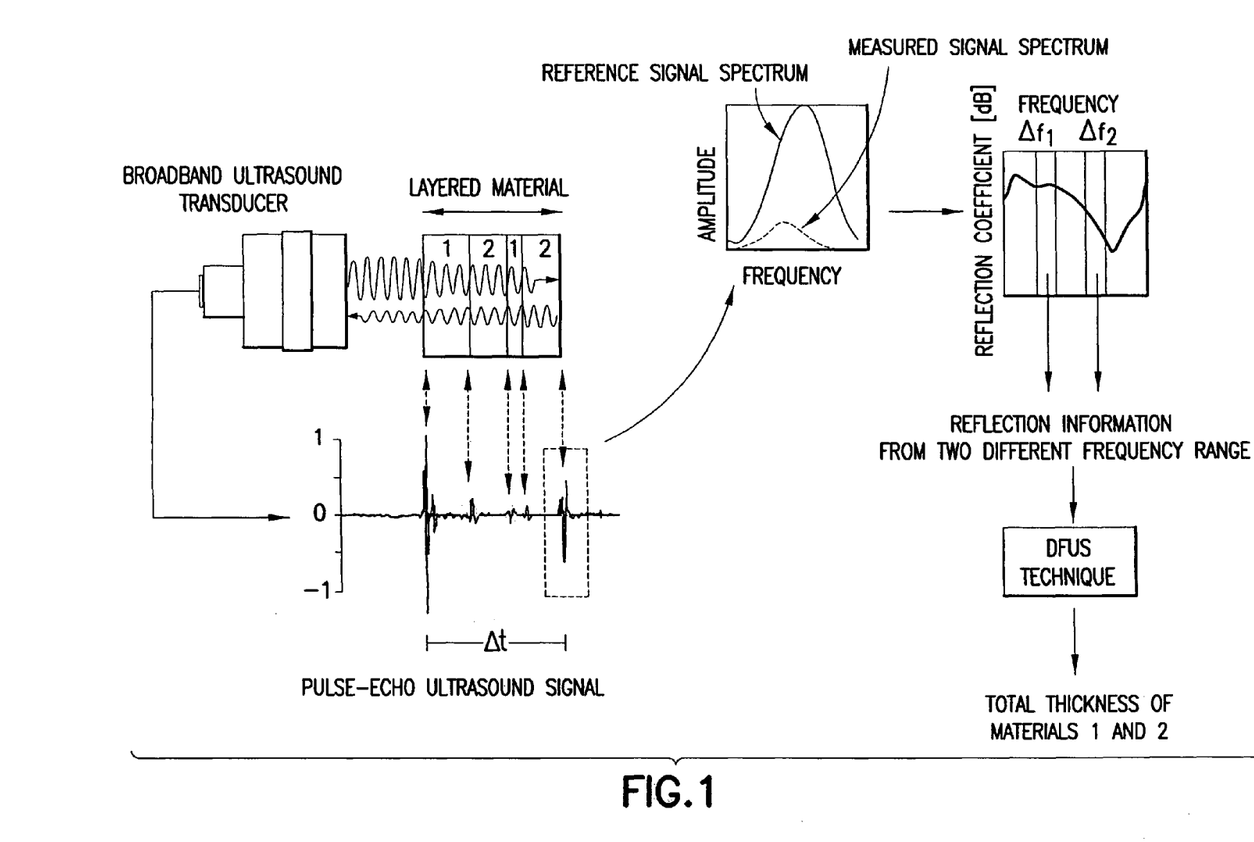
FIG. 1 shows a schematic illustration of measurement with a broadband ultrasound transducer.
Figure 2:
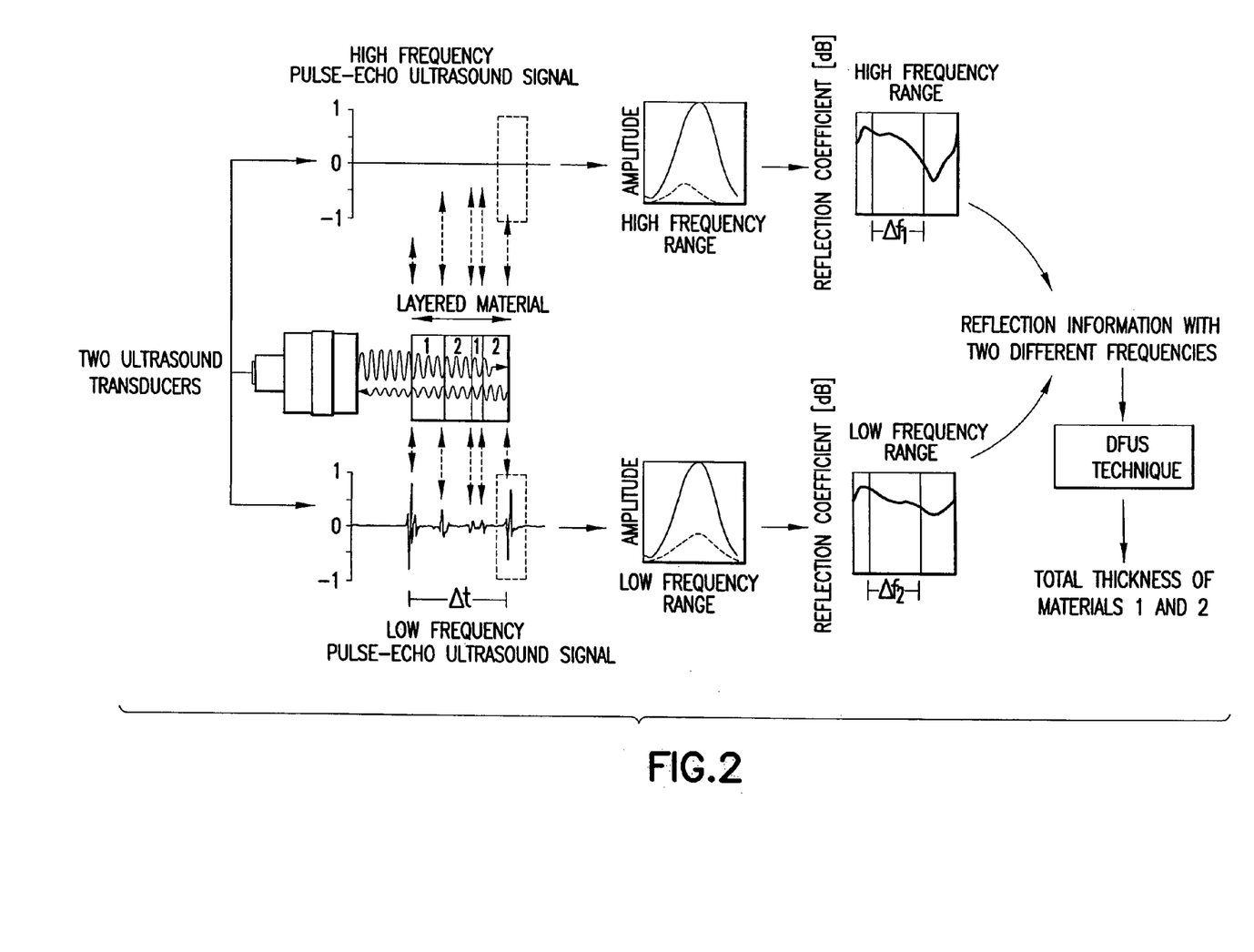
FIG. 2 shows a schematic illustration of measurement with two ultrasound transducers.

In FIG. 2 layered material is measured with two ultrasound transducers with different frequencies. Ultrasound propagates through multilayered material with two different frequencies and ultrasound echo is reflected from the bottom of the multilayer structure. Both low and high frequency pulse-echo signals are recorded for the analysis. The reflection from the bottom of the multilayer material for each signal (low and high frequency) is used. Frequency responses (frequency spectrum) of the ultrasound signals are calculated using the fast Fourier transform (FTT) algorithm in both cases. Same algorithm is used to calculate frequency spectrum of the reference pulse-echo measurement from the standardized reflector. The representative frequency range is determined for the low ($\Delta f2$) and high ($\Delta f1$) ultrasound frequency measurement. At low and high frequencies, reflection coefficients are calculated as a ratio between the frequency spectra of the ultrasound reflection from the bottom of the material and reference reflector, respectively. Both reflection coefficient spectra (for low and high frequencies) are used at the determined frequency ranges ($\Delta f1$ and $\Delta f2$) in the DFUS-based thickness calculation. Finally, using the DFUS technique, total thicknesses of material 1 and 2 can be determined.

Figure 3:
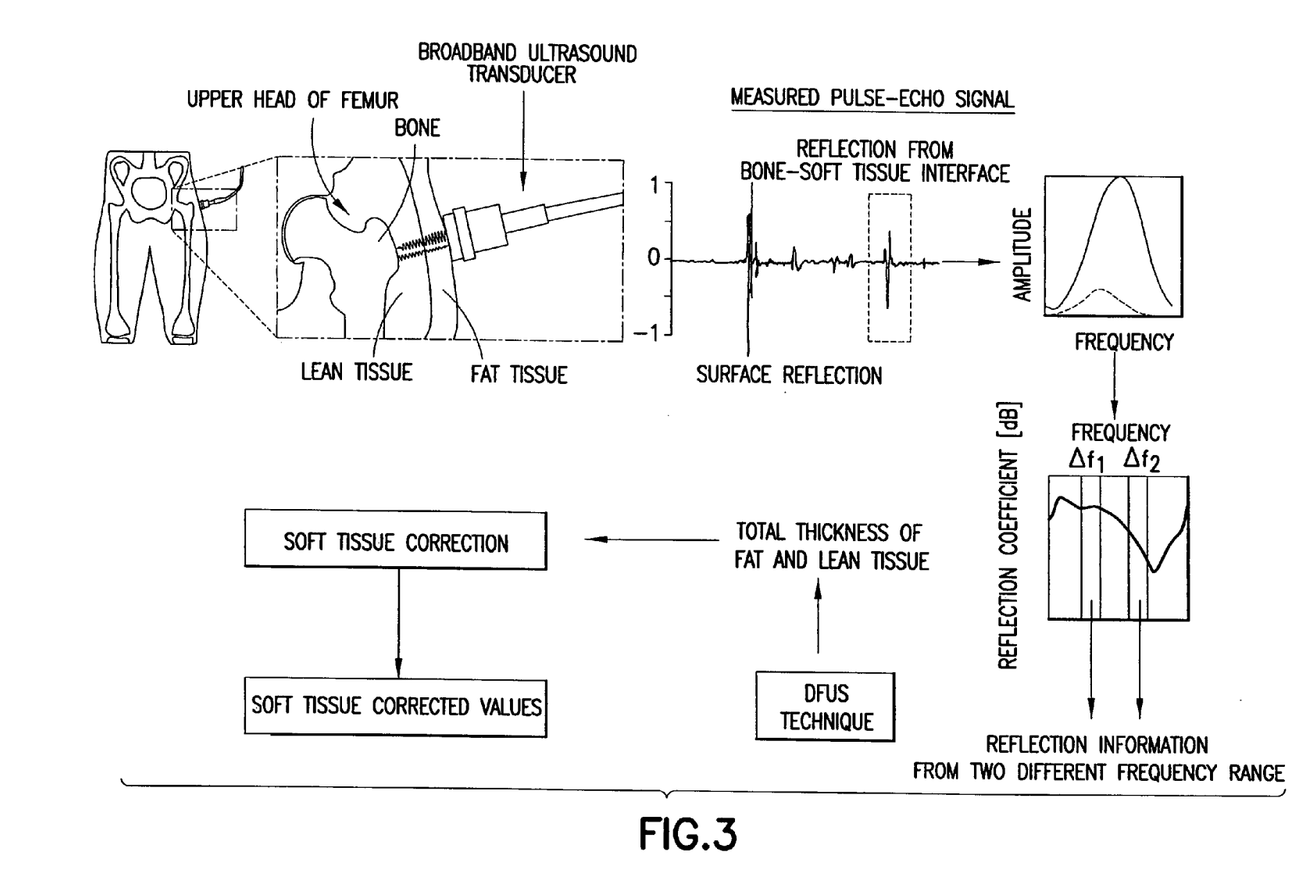
FIG. 3 shows a schematic illustration of measurement of total thickness of layered adipose and lean tissues with a broadband ultrasound transducer.

In FIG. 3 total thicknesses of the adipose and lean tissues are determined with DFUS-technique. First, ultrasound signal is transmitted through soft tissue. Ultrasound is reflected from the soft tissue-bone interface. Measured pulse-echo signal is recorded and saved for the subsequent analysis. The frequency spectrum of the interface reflection (soft tissue-bone) is calculated using fast Fourier transform (FFT) algorithm. Subsequently, calculated frequency spectrum is compared to frequency spectrum of the reference measurement (pulse-echo measurement of the standardized reflector, e.g. polished steel plate). When using a single broadband transducer, the reflection coefficients at two representative frequencies are determined. Finally, the DFUS-technique is used to calculate the total thicknesses of the adipose and lean tissues. Using the information on these thicknesses, soft tissue effect on the ultrasound measurement of the bone can be mathematically eliminated. Finally, soft tissue corrected values of the bone parameters are calculated.

EXAMPLE 1

Summary

Quantitative ultrasound has been suggested to have potential for clinical screening of osteoporosis. Most commercial ultrasound devices are based on through-transmission measurement of calcaneus, which is not a common fracture site. In contrast to through-transmission measurements, reflection and backscattering measurements may be conducted at typical fracture sites such as vertebra and proximal femur. Soft tissues overlying bones at these regions affect reliability of the measurements. In this example 1, the dual frequency ultrasound technique (DFUS) for elimination of the soft tissue induced errors is presented. The technique is preliminary validated with elastomer samples. For further validation, human trabecular bone samples (n=25) covered with heterogeneous soft tissues are measured at frequencies of 2.25 MHz and 5.0 MHz. The DFUS-technique reduced (p<0.01) the mean soft tissue induced error in broadband ultrasound backscattering and in integrated reflection coefficient (at 5.0 MHz) from 58.6% to −4.9% and from 127.4% to 23.8%, respectively. To conclude, the dual frequency ultrasound technique being the first ultrasound technique capable of determining the composition and thickness of overlying soft tissue, may enhance the accuracy of clinical ultrasound measurements and have significant clinical value.

Methods—Validation with Elastomer Samples.

Three acoustically different elastomers (3a-c, Teknikum Oy, Vammala, Finland, diameter=26 mm) were used in the investigations. The thicknesses of elastomers 3a, 3b and 3c were 10.25 mm, 5.50 mm and 6.00 mm, respectively. The elastomer samples (elastomer 3, FIG. 4) were measured with and without the overlying interfering combinations of elastomer 1 and 2 (FIG. 4) (RAPRA Technology Ltd, Shropshire, UK).

Figure 4:
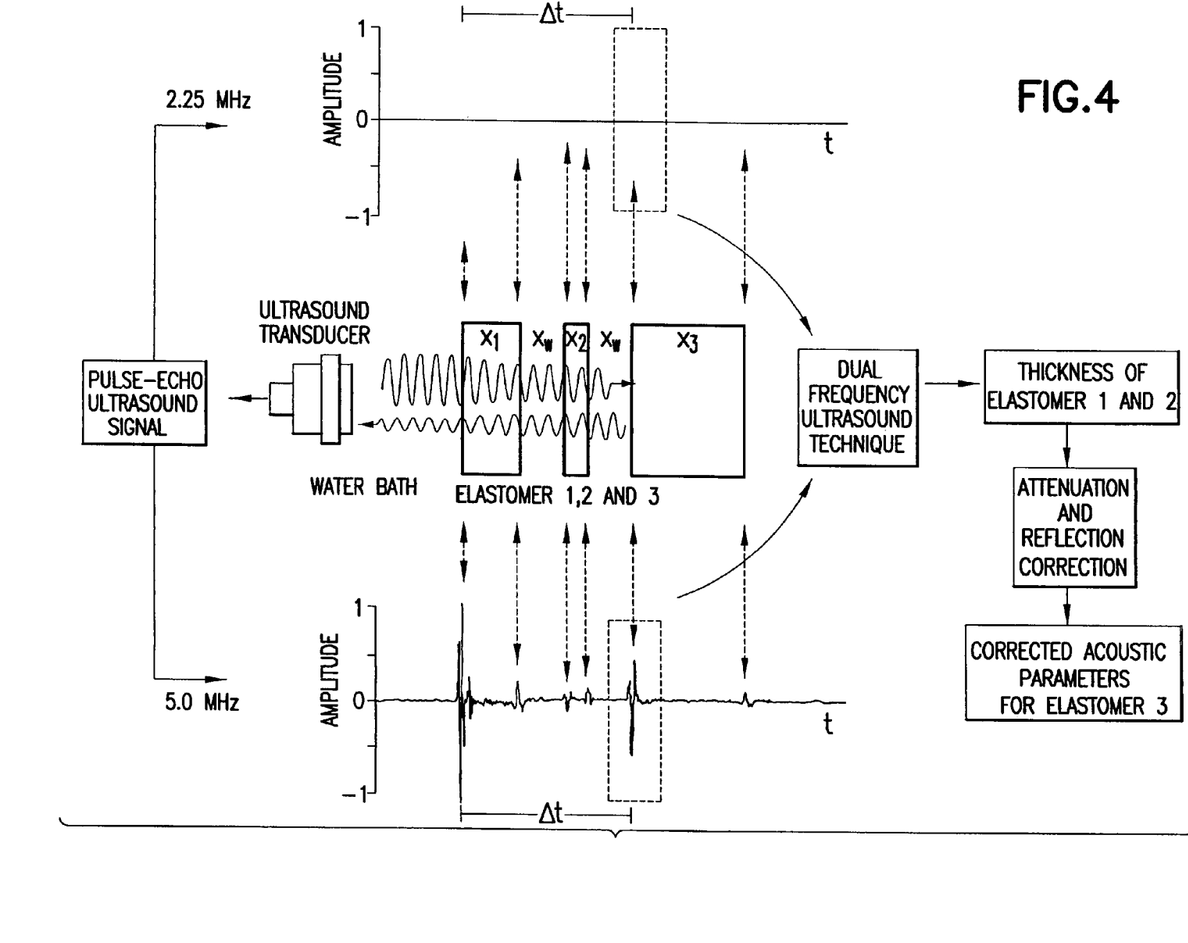
FIG. 4 shows a schematic illustration of the measurement of total thickness of three acoustically different elastomers in accordance with the example 1.

FIG. 4 shows an experimental set-up for acoustic measurements of elastomer samples. Region of interest in ultrasound signal is located at the echo arising from surface of elastomer 3. The dual frequency ultrasound technique was used to minimize the artifacts induced by the elastomers 1 and 2 in determination of acoustic properties of elastomer 3.

As shown in FIG. 4, layered elastomer material is measured with two ultrasound transducers with different frequencies. Ultrasound propagates through multilayered elastomers with two different frequencies and signals reflect from the surface of the elastomer 3. Both low and high frequency pulse-echo signals are recorded for the analysis. The reflection from the surface of elastomer 3 is used for each signal (low and high frequency). Frequency response (frequency spectrum) of the ultrasound signals is calculated using the fast Fourier transform (FTT) algorithm in both cases. Same algorithm is used to calculate frequency spectrum of the reference pulse-echo measurement from the standard reflector (i.e. polished steel plate) using transducer-steel plate distance corresponding the distance of transducer-elastomer 3. The representative frequency range is determined for the low (2.25 MHz) and high (5.0 MHz) ultrasound frequency measurement. At low and high frequencies, reflection coefficients are calculated as a ratio between frequency spectra of the ultrasound reflection from the surface of elastomer 3 and reference reflector, respectively. Both reflection coefficient spectra (for low and high frequencies) are used at the DFUS-based thickness calculation. Finally, using the DFUS technique, total thicknesses of elastomer 1 and 2 can be determined. The dual frequency ultrasound technique was used to minimize the artifacts induced by the elastomers 1 and 2 in determination of acoustic properties of elastomer 3.

The interfering elastomer combinations (n=3, diameter=15 mm) consist of two different elastomer samples of various thicknesses (elastomers 1 and 2, FIG. 4). Thicknesses of elastomers were measured with a micrometer. Thicknesses of elastomers 1 and 2 in the interfering elastomer combinations were 1.19 mm and 3.22 mm (combination 1), 2.00 mm and 1.85 mm (combination 2) and addition 3.01 mm and 0.97 mm (combination 3), respectively. Elastomers 1 and 2 have mechanical shore values of 40 and 69, respectively.

Methods—Validation with Living Tissues.

Human trabecular bone samples (n=25) were measured with and without the overlying porcine soft tissues (n=25). Human trabecular bone samples (diameter=16 mm, thickness=7.5 mm), were harvested from the human femoral lateral condyles (n=13) and tibial lateral plateaus (n=12) (National Authority for Medicolegal Affairs, permission 1781/32/200/01). Fresh soft tissue samples (thickness=10-20 mm), provided by the local slaughterhouse (Atria Oy, Kuopio, Finland), were prepared just before the measurements from porcine soft tissue having fat content of 30%.

Ultrasound Measurements

Center frequencies of ultrasound transducers were 2.25 MHz and 5.0 MHz. All ultrasound measurements of elastomers were conducted in distilled degassed water bath (21° C.). Ultrasound speed and average attenuation in elastomers 1 and 2 were determined with the substitution method in through-transmission geometry whereas the integrated reflection coefficient (IRC) was determined with the pulse-echo technique. Ultrasound average attenuation and IRC for elastomers 3a-c were determined with and without the interfering overlying elastomer combinations. The acoustic properties of adipose (fat) and lean tissues as well as of human trabecular bone were determined at frequencies of 2.25 MHz and 5.0 MHz. The above mentioned measurements with living tissues (adipose and lean tissues, trabecular bone) were conducted in degassed phosphate buffered saline (PBS) at body temperature (37° C.).

Dual Frequency Ultrasound Technique

Ultrasound average attenuation and IRC were determined for elastomers 3a-c with and without the interfering overlying elastomers. For elimination of the artifacts induced by the interfering elastomers, their thicknesses and acoustic properties must be known. The thicknesses of the interfering elastomer layers can be determined using the dual frequency ultrasound technique.

The corrected IRC ($IRC_{corr}$) can be determined as follows:

$$IRC_{corr} = IRC_{uncorr} + 2x_1\alpha_1 + 2x_2\alpha_2 + K_i, \quad (1)$$

where $IRC_{uncorr}$ is uncorrected integrated reflection coefficient (IRC), x is elastomer thickness and $\alpha$ is ultrasound average attenuation coefficient for elastomer. Subscripts 1 and 2 refer to elastomers 1 and 2, respectively. $K_i$ is correction factor for compensation of ultrasound reflections at surfaces of elastomers 1 and 2:

$$K_i = 8.68 \ln((1-R_1^2)^2(1-R_2^2)^2) \quad (2)$$

where $R_i$ is corresponding reflection coefficient of elastomers 1 and 2 (subscripts 1 and 2, respectively). The corrected average attenuation ($A_{corr}$) can be determined as follows:

$$A_{corr} = A_{uncorr} - x_1\alpha_1 - x_2\alpha_2 - K_a, \quad (3)$$

where $A_{uncorr}$ is the uncorrected average attenuation and $K_a$ is correction factor for compensation for ultrasound reflections at surfaces of elastomers 1, 2 and 3.

$$K_a = 8.68 \ln((1-R_1^2)(1-R_2^2)(1-R_3^2)). \quad (4)$$

Soft tissue correction for IRC and broadband ultrasound backscattering (BUB) measurements of bone-soft tissue combinations was conducted similarly as for elastomers (equation 1). Since no clear acoustic boundaries did existed in heterogeneous mixture of lean and adipose tissue, the $K_i$ term could be neglected.

Results and Conclusions

Elastomer 2 showed higher average attenuation and IRC compared to elastomer 1, whereas variation of speed of sound (SOS) in the elastomers 1 and 2 was only minor (Table 1).

Average attenuation and IRC increased as a function of frequency in both elastomers (Table 1). SOS was higher and average attenuation lower in lean tissue as compared to adipose tissue (Table 2). As expected, average attenuation increased as a function of frequency in lean and adipose tissues (Table 2).

TABLE 1

Values (Mean ± SD) of integrated reflection coefficient (IRC), speed of sound (SOS) and average attenuation of elastomers 1 and 2 at 2.25 MHz and 5.0 MHz. In dual frequency ultrasound technique, the mean values of acoustic properties of elastomers 1 and 2 were used to eliminate their interfering effect when in the determination values of acoustic parameters for elastomer 3 (FIG. 4).

|  | 2.25 MHz | | 5.0 MHz | |
| --- | --- | --- | --- | --- |
|  | Elastomer 1 | Elastomer 2 | Elastomer 1 | Elastomer 2 |
| IRC (dB) | −25.5 ± 1.5 | −14.5 ± 0.6 | −18.7 ± 1.6 | −10.2 ± 0.2 |
| SOS (m/s) | 1553 ± 43 | 1586 ± 26 | 1553 ± 43 | 1586 ± 26 |
| Average attenuation (dB/cm) | 7.2 ± 1.4 | 26.9 ± 4.7 | 21.0 ± 0.6 | 66.7 ± 3.8 |

TABLE 2

Values (mean ± SD) of speed of sound (SOS) and average attenuation of lean and adipose (fat) tissue at 2.25 MHz and 5.0 MHz. In dual frequency ultrasound technique, the mean values were used to eliminate the interfering effect of overlying soft tissue in the determination of values of acoustic parameters for trabecular bone tissue.

|  | 2.25 MHz | | 5.0 MHz | |
| --- | --- | --- | --- | --- |
|  | Lean tissue | Adipose tissue | Lean tissue | Adipose tissue |
| SOS (m/s) | 1596 ± 21 | 1446 ± 32 | 1596 ± 21 | 1446 ± 32 |
| Average attenuation (dB/cm) | 0.9 ± 1.0 | 1.5 ± 1.5 | 2.1 ± 1.6 | 4.7 ± 2.2 |

The DFUS-technique reduced the mean error, induced by interfering elastomers, in IRC and average attenuation (at 2.25 MHz) from 37.5-77.5% to −12.0-4.9% and from 70.0-201.1% to −1.1-34.6%, respectively (Table 3). At higher frequency (5.0 MHz), the DFUS-technique reduced the mean error, induced by interfering elastomers, in IRC and in average attenuation from 103.6-289.4% to −15.9-5.6% and from 33.8-158.3% to −29.7-6.5%, respectively (Table 3)

TABLE 3

Values of integrated reflection coefficient (IRC) and average attenuation of elastomers (3a-c) at 2.25 MHz and 5.0 MHz. The values of acoustic parameters for elastomers 3a-c were also determined with interfering overlying elastomers (1 and 2) present (FIG. 4). Uncorrected (mean ± SD) as well as corrected values (dual frequency ultrasound technique) are also presented. Absolute errors are calculated using the mean values of parameters.

|  | 2.25 MHz | | | 5.0 MHz | | |
| --- | --- | --- | --- | --- | --- | --- |
|  | Elastomer 3a | Elastomer 3b | Elastomer 3c | Elastomer 3a | Elastomer 3b | Elastomer 3c |
| IRC (dB) Average attenuation (dB/cm) Uncorrected values | −35.7 10.5 | −18.7 17.1 | −20.1 6.1 | −31.7 30.0 | −14.1 42.8 | −19.3 17.8 |
| IRC (dB) Average attenuation (dB/cm) Corrected values | −49.0 ± 2.7 17.8 ± 1.7 | −33.2 ± 3.4 33.2 ± 4.3 | −31.4 ± 1.7 18.4 ± 1.7 | −64.5 ± 2.7 40.1 ± 1.6 | −55.0 ± 5.5 72.3 ± 4.3 | −49.6 ± 4.8 46.1 ± 6.0 |
| IRC (dB) Average attenuation (dB/cm) Error for uncorrected values | −37.4 ± 2.8 11.8 ± 1.7 | −16.5 ± 2.8 16.9 ± 4.5 | −20.2 ± 0.9 8.2 ± 0.6 | −33.4 ± 2.8 24.0 ± 1.9 | −11.9 ± 2.8 30.1 ± 4.5 | −19.4 ± 0.9 19.0 ± 1.9 |
| IRC (%) | 37.5 | 77.5 | 56.7 | 103.6 | 289.4 | 157.2 |
| Average attenuation (%) Error for corrected values | 70.0 | 94.0 | 201.1 | 33.8 | 68.9 | 158.3 |
| IRC (%) | 4.9 | −12.0 | 0.7 | 5.6 | −15.9 | 0.8 |
| Average attenuation (%) | 12.9 | −1.1 | 34.6 | −19.9 | −29.7 | 6.5 |

In soft tissue-bone combination, the DFUS-technique reduced the mean soft tissue induced error in BUB and in IRC (at 5.0 MHz) from 58.6% to −4.9% and from 127.4% to 23.8%, respectively (Table 4).

TABLE 4

Values (mean ± SD) of integrated reflection coefficient (IRC) and broadband ultrasound backscattering (BUB) in human trabecular bone at 2.25 MHz and 5.0 MHz. The acoustic properties of bone samples were also determined with overlying soft tissue layers. Uncorrected (mean ± SD) as well as corrected values (dual frequency ultrasound technique) are also presented. Absolute errors are calculated using the mean values of parameters.

|  | Trabecular bone (n = 26) | |
| --- | --- | --- |
|  | 2.25 MHz | 5.0 MHz |
| IRC (dB) | −10.1 ± 2.8 | −10.1 ± 3.1 |
| BUB (dB) | −15.5 ± 4.3 | −16.5 ± 3.8 |
| Uncorrected values | | |
| IRC (dB) | −16.4 ± 4.0 | −22.9 ± 5.6 |
| BUB (dB) | −22.1 ± 4.8 | −26.1 ± 6.3 |
| Corrected values | | |
| IRC (dB) | −12.5 ± 4.0 | −12.5 ± 4.0 |
| BUB (dB) | −18.1 ± 4.1 | −15.7 ± 4.8 |
| Error for uncorrected values | | |
| IRC (%) | 62.4 | 127.4 |
| BUB (%) | 42.5 | 58.6 |
| Error for corrected values | | |
| IRC (%) | 23.3 | 23.8 |
| BUB (%) | 17.0 | −4.9 |

In this example 1, a new ultrasound method for soft tissue correction of bone ultrasound measurement is introduced. The initial validation with elastomer samples demonstrated significant improvement in accuracy of ultrasound measurements. The error of IRC at 5.0 MHz diminished from 103.6-289.4% to −15.9-5.6%. Similarly, with human trabecular bone samples with 10-20 mm of overlying soft tissue the error in BUB (at 5.0 MHz) diminished from 58.6% to −4.9%.

To conclude, DFUS-technique introduced in this example 1 is the first ultrasound technique capable of determining the amount and composition of overlying soft tissue and thus may enhance accuracy of clinical ultrasound measurements significantly.

APPENDIX FOR EXAMPLE 1

Thickness of interfering layers 1 and 2 can be solved with the dual frequency ultrasound technique. Ultrasound reflection amplitudes of low and high frequency ultrasound ($A_l, A_h$) from the first surface of the region of interest (e.g. bone or elastomer 3 (FIG. 4)), can be expressed as follows:

$$A_l = H_l e^{-2\alpha_{1,l} x_1} e^{-2\alpha_{2,l} x_2} A_{0,l}, \tag{A1}$$

$$A_h = H_h e^{-2\alpha_{1,h} x_1} e^{-2\alpha_{2,h} x_2} A_{0,h}, \tag{A2}$$

where H is reflection term including ultrasound reflections at surfaces of interfering layers, α is attenuation coefficient and x is thickness of interfering layer. Subscripts 1 and 2 and l and h refer to interfering layers 1 and 2 and low and high ultrasound frequencies, respectively. Ultrasound amplitudes $A_{0,l}$ and $A_{0,h}$ refer to ultrasound reflection amplitudes from polished steel plate with low and high frequencies, respectively. If ultrasound reflection coefficient at surfaces of interfering layers or at surface of the sample is frequency dependent, it must consider during calculations:

$$H_l = m(H_h)^k, \tag{A3}$$

where coefficients m and k denotes the frequency dependence of the reflection term. Ultrasound reflection amplitude $A_l$ can now be expressed as:

$$A_l = m\left(\frac{A_h}{A_{0,h}} e^{2(\alpha_{1,h} x_1 + \alpha_{2,h} x_2)}\right)^k e^{-2\alpha_{1,l} x_1} e^{-2\alpha_{2,l} x_2} A_{0,l}. \tag{A4}$$

By substituting:

$$S = 2k\alpha_{1,h} - 2\alpha_{1,l}, \tag{A5}$$

$$J = 2k\alpha_{2,h} - 2\alpha_{2,l}, \tag{A6}$$

equation A4 can be expressed as follows:

$$\frac{A_l (A_{0,h})^k}{m(A_h)^k A_{0,l}} = e^{x_1 S + x_2 J} \tag{A7}$$

The time difference Δt between the reflections from the first surface of interfering layer and the surface of the sample (see FIG. 4) can be written as follows:

$$\Delta t = 2\left(\frac{x_1}{c_1} + \frac{x_2}{c_2} + \frac{2x_w}{c_w}\right), \tag{A8}$$

where $c_1$, $c_2$ and $c_w$ are the average sound speeds measured at low and high ultrasound frequencies. The subscript w refers to water. Thickness of interfering layer 1 can be expressed as:

$$x_1 = \left(\frac{\Delta t}{2} - \frac{x_2}{c_2} - \frac{2x_w}{c_w}\right) c_1. \tag{A9}$$

Thickness of interfering layer 2 can now be solved from equations A7 and A9:

$$x_2 = \frac{\ln\left(\frac{1}{m}\right) + \ln\left(\frac{A_l}{A_{0,l}}\right) - k\ln\left(\frac{A_h}{A_{0,h}}\right) - \left(\frac{\Delta t}{2} - \frac{2x_w}{c_w}\right) c_1 S}{J - \frac{c_1 S}{c_2}} \tag{A10}$$

Finally, using the determined thickness of layer 2, the thickness of layer 1 can be calculated from equation A9

In bone—soft tissue combination, thickness of adipose (fat) and lean tissue can be solved with dual frequency ultrasound technique. Reflection at bone surface was found to be frequency independent (2.25 MHz vs. 5.0 MHz and the reflection from the soft tissue surface and adipose-lean tissue interfaces were found to be minimal, thus m=1 and k=1. Since there is no free water ($x_w$=0) between adipose (fat) and lean tissue, the equation A8 can be simplified and the lean tissue thickness can be expressed as:

$$x_2 = \frac{\ln\left(\frac{A_l}{A_{0,l}}\right) - \ln\left(\frac{A_h}{A_{0,h}}\right) - \left(\frac{\Delta t}{2}\right)c_1 S}{J - \frac{c_1 S}{c_2}}, \quad \text{(A11)}$$

where subscripts 1 and 2 refer to adipose and lean tissues, respectively.

EXAMPLE 2

Summary

Quantitative ultrasound has been suggested to have potential for clinical screening of osteoporosis. However, most commercial ultrasound devices are based on through-transmission measurement of calcaneus, which is not a common fracture site. In contrast to through-transmission measurements, reflection and backscattering measurements may be conducted at typical fracture sites such as vertebra, radius and proximal femur. Unfortunately, soft tissues overlying bones at these regions diminish reliability of the measurements. In this example 2, the dual frequency ultrasound (DFUS) technique is applied for in vivo elimination of the soft tissue induced errors from integrated reflection coefficient (IRC) measurements of human distal femur. The ability of the technique to follow changes in local soft tissue composition is investigated in vivo with a dieting body builder. Furthermore, a novel single transducer application of the technique is presented.

The single broadband ultrasound transducer DFUS-technique proved to be an accurate method for determination of local soft tissue composition as verified by reference, i.e. dual energy x-ray absorptiometry (DXA) measurements ($r^2$=0.88). The DFUS corrected IRC values showed only minor variation during the diet, despite significant changes in quantity and composition of overlying soft tissue were detected. This result is encouraging as the control DXA measurements showed that dieting did not have an affect on bone density.

To conclude, the dual frequency ultrasound technique being straightforward, but accurate technique for determination of the composition and thickness of overlying soft tissue layer, may enhance the accuracy of clinical ultrasound measurements of bone quality and, thus, have a significant clinical value. Moreover, the technique have proven to be fast and accurate tool for local soft tissue characterization (i.e. composition) as confirmed with reference measurements (DXA).

Materials and Methods

A volunteer bodybuilder (one of the authors, age=27 years, height=172 cm, starting weight=92 kg) had a pre-competition 21-week low energy diet in order to reduce body fat content with minimal concurrent loss of lean tissue. Written consent was obtained from the volunteer. The morning weight of the volunteer was measured weekly, in standardized manner, with a digital scale. Total relative body fat and soft tissue composition at the region of interest (ROI) located at right distal thigh were determined every three weeks with DXA (Lunar Prodigy, Wessling, Germany). Fluid and food intake was kept minimal for more than 2 hours prior to DXA measurement. Moreover, ultrasound measurements of ROI located at right thigh of the volunteer were conducted in a standardized manner every three weeks together with the DXA measurements.

All ultrasound measurements (UltraPAC, Physical Acoustic Co., NJ, USA) were conducted manually with two focused transducers (centre frequencies 2.25 MHz and 5 MHz and focal distances 50.3 and 49.8 mm, respectively. Panametrics Inc., Waltham, Mass., USA). Acoustic coupling was assured by using ultrasound gel (Aquasonic 100, Parker Laboratories Inc, Fairfield, N.J., USA).

The dual frequency ultrasound technique (DFUS) is based on measurement of integrated reflection coefficient (IRC) at soft tissue—bone interface at two ultrasound frequencies. Integrated reflection coefficient (IRC) was calculated as follows $$IRC = \frac{1}{\Delta f} \int_{\Delta f} R(f) df, \quad (1)$$

where $\Delta f$ is the effective frequency range and $R(f)$ is the ultrasound reflection coefficient spectrum at the soft tissue—bone interface.

As the ultrasound reflection at soft tissue—bone interface is frequency independent and as the frequency dependent attenuation coefficients are known for lean and adipose (fat) tissues, the soft tissue composition can be determined with the DFUS technique. In following the mathematical basis of the DFU technique is briefly presented.

The corrected IRC ($IRC_{corr}$) can be determined as follows:

$$IRC_{corr} = IRC_{uncorr} + 2x_L\alpha_L + 2x_A\alpha_A, \quad (2)$$

$IRC_{uncorr}$ is uncorrected IRC, x is tissue thickness, $\alpha$ is ultrasound average attenuation and subscripts L and A refer to lean and adipose tissues, respectively.

Thicknesses of lean and adipose tissue layers $x_L$ and $x_A$ can be solved with the dual frequency ultrasound technique.

Briefly, lean tissue thickness can be expressed as:

$$x_L = \frac{\ln\left(\frac{A_l}{A_{0,l}}\right) - \ln\left(\frac{A_h}{A_{0,h}}\right) - \left(\frac{\Delta t}{2}\right)c_L(2\alpha_{L,h} - 2\alpha_{L,l})}{(2\alpha_{A,h} - 2\alpha_{A,l}) - \frac{c_L(2\alpha_{L,h} - 2\alpha_{L,l})}{c_A}}. \quad (3)$$

Thickness of adipose tissue can be expressed as:

$$x_A = \left(\frac{\Delta t}{2} - \frac{x_L}{c_L}\right)c_A, \quad (4)$$

where subscripts A and L refer to adipose and lean tissues, respectively.

Figure 5A:
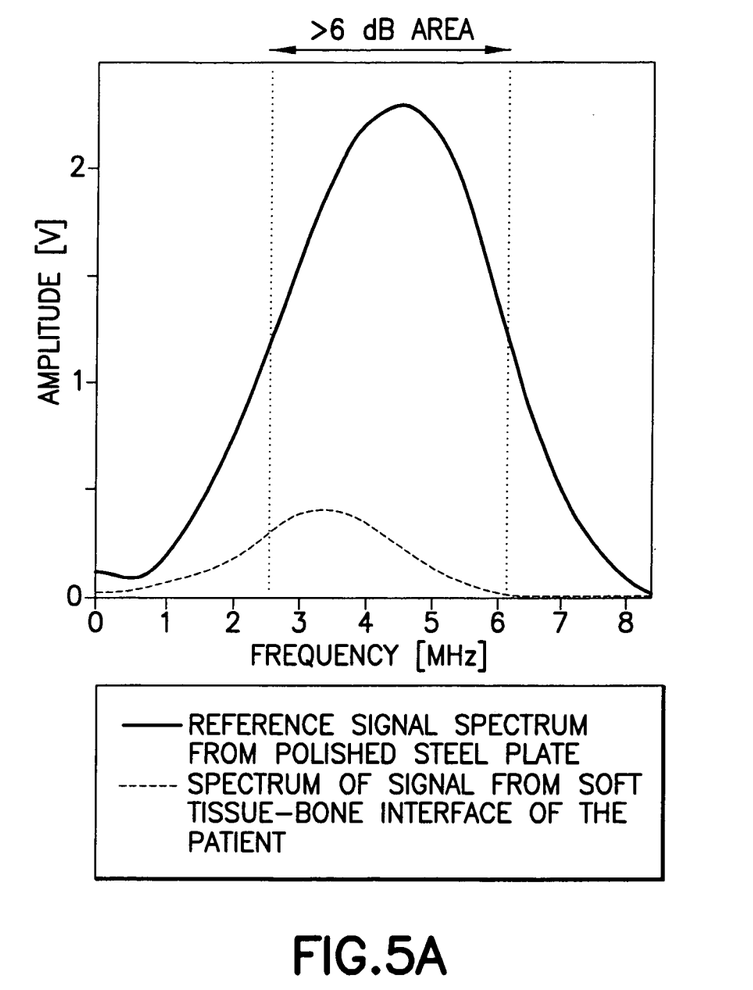
FIG. 5a shows an effective frequency band, which is determined from the reference signal spectrum in accordance with the example 2.
Figure 5B:
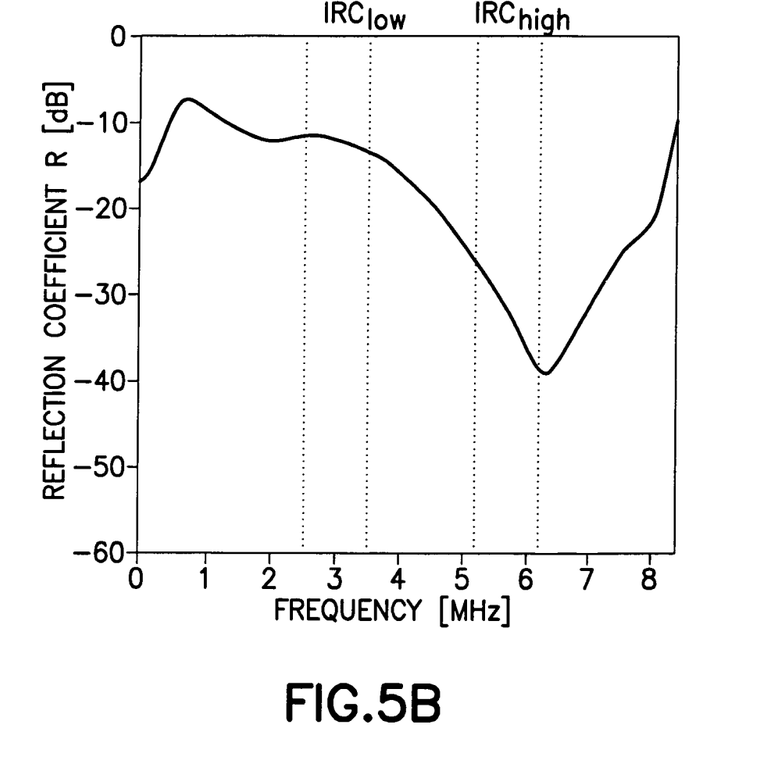
FIG. 5b shows how frequency bands for computation of high and low frequency integrated reflection coefficients are obtained in accordance with the example 2.

In the one transducer approach, integrated reflection coefficients for the computational frequency bands of high and low frequency are determined as 1 MHz wide frequency bands at the low and high frequency ends of the transducer effective bandwidth (FIG. 5). The effective (−6 dB) bandwidths of 2.25 MHz and 5 MHz transducers were (1.7-3.9 MHz) and (2.5-6.2 MHz), respectively. The ROI for reflection signal in time domain was windowed with hamming window (length 2 ms) prior to the frequency domain analysis Ultrasound attenuation coefficients for lean and adipose (fat) tissues have previously been determined experimentally for five different frequencies. In the current example, an exponential fit was applied to that data to interpolate attenuation coefficients for frequency bands applied in the present example.

Customized Labview (v.6i, National Instruments, Austin, Tex., USA) and Matlab (Matlab 6.5, The Mathworks Inc., Natick, Mass., USA) functions were constructed for measurements and data analysis, respectively. SPSS version 11.5 (SSPS Inc., Chicago, Ill., USA) was used for statistical analyses. Pearson's correlation analysis was used to calculate linear correlation coefficients.

Results and Conclusions

Figure 6:
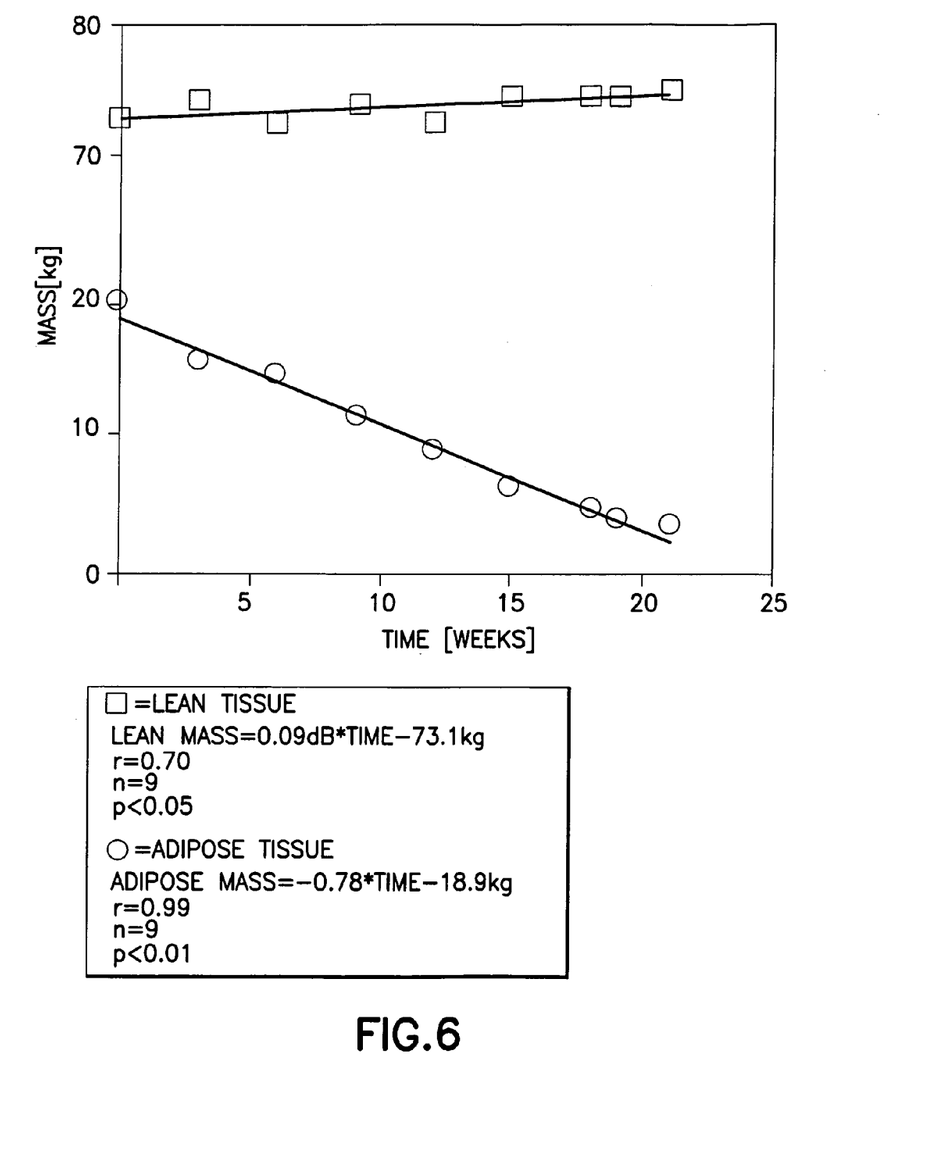
FIG. 6 shows the changes in body composition during the diet as measured with DXA in accordance with the example 2.

During the 21 weeks of dieting the weight of the bodybuilder reduced linearly from 91.6 kg to 75.1 kg ($r^2$=0.99, n=22). Local body fat content in ROI showed similar linear decrease with both DXA and DFU techniques. Moreover, there was no concurrent reduction in total lean tissue mass as determined with DXA (FIG. 6). Importantly, neither the femoral or spinal BMD nor the BMD at ROI were changed during the diet (p=0.87, p=0.64 and p=0.16 respectively).

Significant association was found between DXA and DFUS determined local soft tissue compositions were observed (FIG. 7). Importantly, the single transducer DFUS (at 5 MHz) provided better estimate on local soft tissue composition than the two transducer approach. The non-corrected IRC showed clear growing trend during the diet as the attenuation diminished due to the decrease in fat content (FIG. 8). After soft tissue correction IRC values showed only minor increasing trend during the diet. Importantly, at all frequencies the corrected IRC values showed only a weak trend (not significant) and a small variation (SD=±1.2 dB) throughout the follow up period.

In this example 2 a novel single transducer approach of the dual frequency ultrasound technique was presented for determination of local soft tissue composition. Further, the in vivo applicability of the two and one transducer DFUS approaches was investigated. Both DFUS techniques showed significant potential for in vivo determination of local soft tissue composition. Importantly, the single transducer approach (at 5 MHz) provided more reliable estimation of local soft tissue composition than the original two transducer DFUS technique. This may be explained by single transducer approach being more straightforward requiring only single manual ultrasound measurement.

The non-corrected IRC showed clear growing trend during the diet as the attenuation diminished due to the decrease in fat content. Importantly, after soft tissue correction IRC values showed only minor increasing trend during the diet.

To conclude, the dual frequency ultrasound technique being straightforward, but accurate technique for determination of the composition and thickness of overlying soft tissue layer, may enhance the accuracy of clinical ultrasound measurements of bone quality and, thus, have a significant clinical value. Moreover, the technique have proven to be fast and accurate tool for local soft tissue characterization (i.e. composition) as confirmed with reference measurements (DXA).

FIG. 5a. Time domain pulse-echo signal from the surface of polished steel plate and the surface of bone are transformed to frequency domain spectrums using the fast Fourier transform (FFT) algorithm. The effective frequency band (−6 dB) is determined from the reference signal spectrum.

FIG. 5b. The pulse-echo spectrum measured from the surface of polished steel plate is compared to the pulse-echo spectrum measured from the surface of bone and thus, reflection coefficients as a function of frequency are calculated. The computational frequency bands of high and low frequency for integrated reflection coefficients were determined as 1 MHz wide frequency bands at the low and high frequency ends of the transducer effective frequency band. Corresponding reflection coefficients were used in DFUS calculations.

FIG. 6. Changes in total body composition during the 21-week long diet as measured with DXA. Adipose tissue (fat) mass reduced constantly 780 g every week, whereas mean weekly increase in lean body mass was 90 g.

Figure 7A:
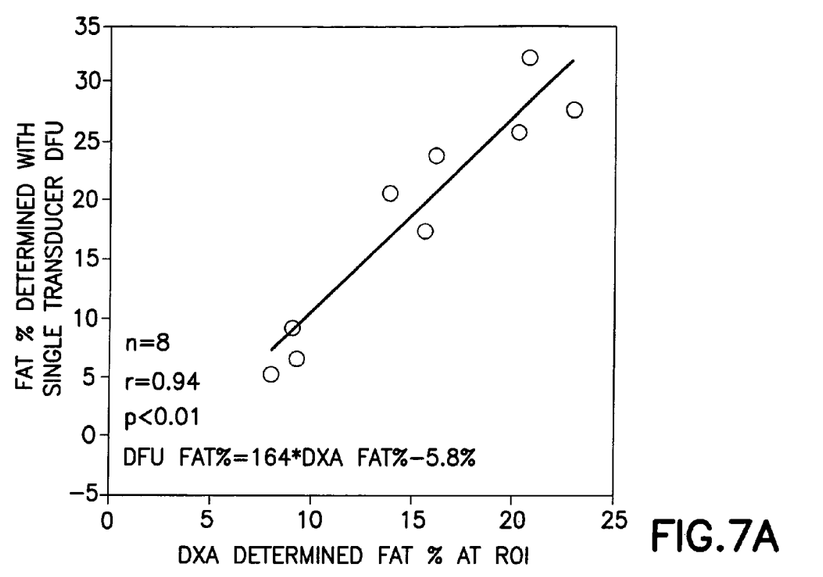
FIG. 7a shows the results using single transducer DFUS method in accordance with the example 2.
Figure 7B:
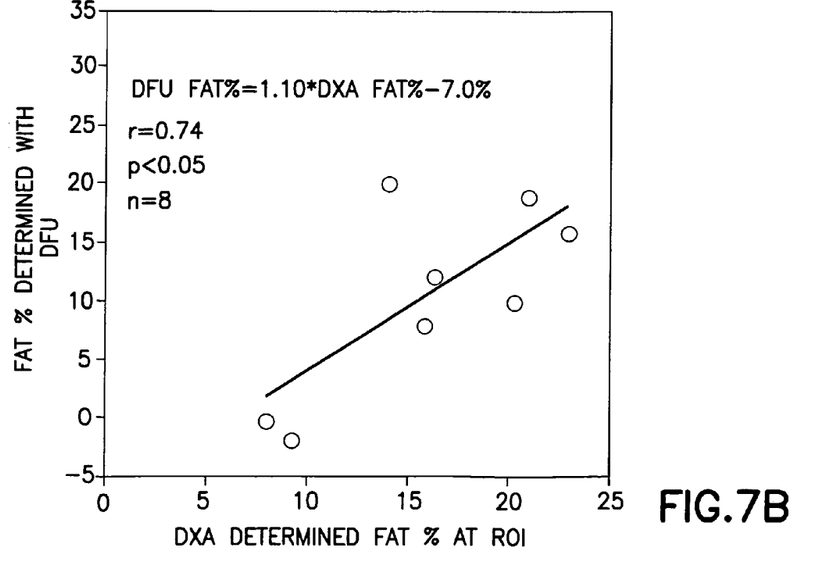
FIG. 7b shows the results using a two-transducer DFUS method in accordance with the example 2.
Figure 8:
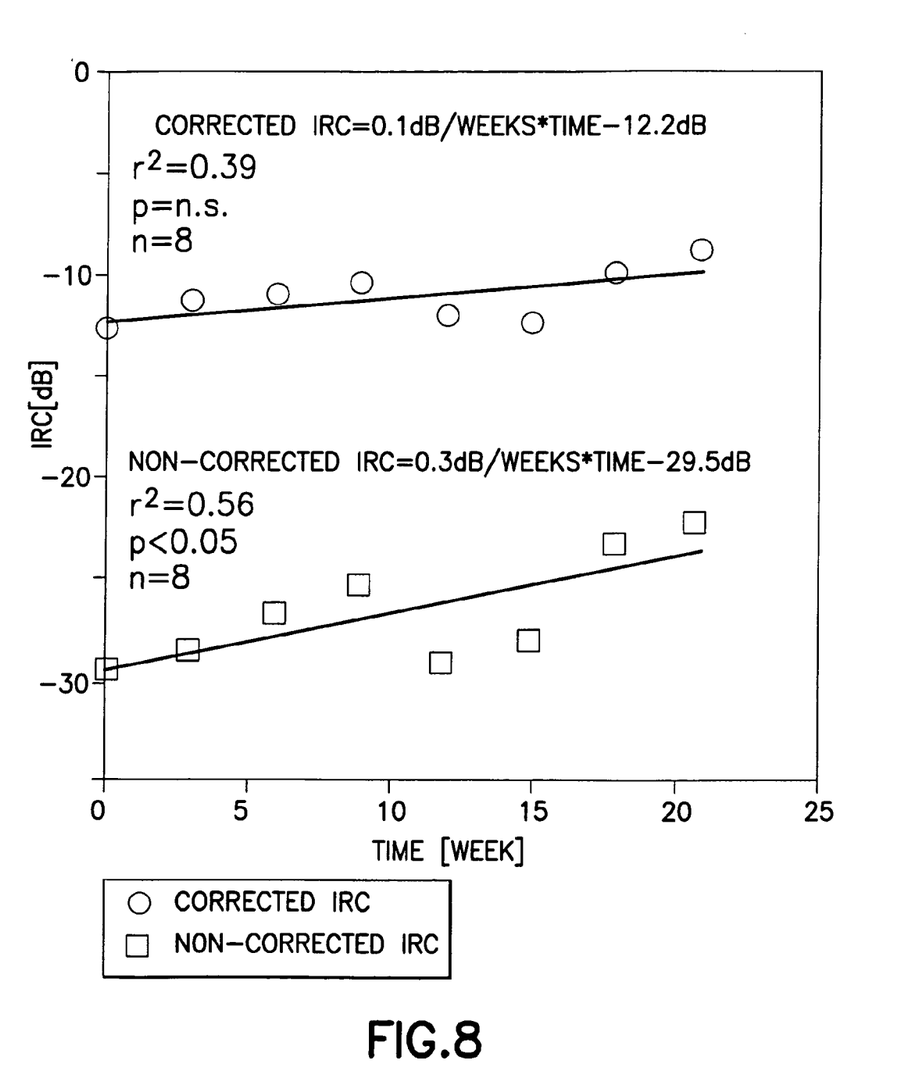

FIG. 7. (a) With DXA technique, local soft tissue composition can be determined. In this study, region of interest was located at right thigh and the local soft tissue composition was determined with DXA- and with DFUS-techniques. The single transducer DFUS method (5 MHz) showed better performance compared to (b) the two-transducer DFUS method.

FIG. 8. Local soft tissue composition within ROI was determined with DFUS technique. Ultrasound reflection coefficient (IRC) from the bone-soft tissue surface was determined with and without DFUS soft tissue correction. Reflection from the bone surface is not expected to change during the diet due to the short follow up time and absence of variation in bone mineral density values as determined from the skeleton during the diet period. Corrected IRC values showed only minor increasing trend (not statistically significant) and small deviation during the diet period where as the non-corrected IRC values showed statistically significant increasing during the follow up.

It will be apparent, that a number of variations can be made to the specifically disclosed embodiments without departing from the true spirit and scope of the invention. Therefore, it is intent of the appended claims to cover all such variations and modifications as come within the scope of the invention.

We claim:

1. A method for measuring thicknesses of materials of a multilayered structure, comprising:
    transmitting one or more ultrasound signals including different frequencies into the multilayered structure, comprising two or more materials, with one or more ultrasound transducers;
    measuring the materials, based on known acoustic properties which are different at the frequencies in use;
    measuring the materials of the multilayered structure, based on speed of sound and attenuation coefficient, wherein the attenuation coefficients are different for materials and frequencies in use;
    measuring and correcting an effect of overlying soft tissue on acoustic measurement of bone by measuring the ultrasound signals reflected from an interface between the soft tissue and the bone with the same one or more ultrasound transducers;
    determining thicknesses of the tissue layers within the overlying soft tissue from the reflected ultrasound signals;
    wherein reflection of the ultrasound signal from the interface of soft tissue and bone is measured, and wherein the time of flight and frequency spectrum of the reflection are calculated,
    wherein frequency spectrum is compared to frequency spectrum of a reference measurement,
    wherein the reflection coefficients from the interface of soft tissue and bone at two or more different frequencies are determined,
    wherein values for speed of sound and attenuation coefficients and measured time of flight and reflection coefficients are used to calculate thicknesses of the tissue layers within the overlying soft tissue structure, and
    using the information on thicknesses of the tissue layers within the overlying soft tissue structure, wherein the soft tissue effect on the ultrasound measurement of the bone is removed and corrected values of the bone parameters are calculated.

2. The method of claim 1, wherein the measuring comprises:
    measuring the total thicknesses of lean and adipose tissues in a multi-layered soft tissue overlying the bone.

3. The method of claim 1, further comprising:
    correcting the effect of total sound attenuation in overlying soft tissues,
    comprising two or more layers of adipose and lean tissues, based on acoustic parameters of the bone.

4. A method for measuring thicknesses of adipose and lean tissues in a soft tissue, comprising:
    transmitting two or more ultrasound signals with different frequencies into the soft tissue consisting of two or more layers of adipose and lean tissues by using two or more ultrasound transducers located over or on the skin surface;
    measuring intensities of two or more ultrasound signals at different frequencies reflected from a surface of a bone with the same two or more ultrasound transducers located over or on the skin surface;
    calculating a frequency spectrum of a reflected ultrasound signal, wherein the frequency spectrum is compared to a frequency spectrum of a reference measurement;
    wherein reflection coefficients from the interface of soft tissue and bone at two or more different frequencies are determined,
    wherein values for speed of sound and attenuation coefficients and measured time of flight and reflection coefficients are used to calculate thicknesses of tissue layers within the soft tissue, and
    using the information on thicknesses of the tissue layers within the soft tissue, wherein the soft tissue effect on the ultrasound measurement of the bone is removed and corrected values of the bone parameters are calculated;
    measuring a time of flight in the soft tissue by subtracting an echo time of the skin surface from an echo time of the bone surface;
    determining the total thickness of the adipose as well as the total thickness of the lean tissue, separately, within soft tissue overlying the bone by using reflection intensity information of two or more ultrasound frequencies and by using the time of flight information in the soft tissue.

5. The method of claim 4, wherein the measuring comprises:
    measuring total thicknesses of adipose and lean tissues, wherein values of attenuation coefficient and speed of sound of the tissues are known at the frequencies in use, and values of attenuation coefficient for adipose and lean tissues are different at the frequencies in use.

6. The method of claim 4, further comprising:
    correcting an effect of total sound attenuation in overlying soft tissues, comprising two or more layers of adipose and lean tissues, based on acoustic parameters of the bone.

* * * * *